United States Patent [19]

Lina et al.

[11] Patent Number: 4,778,915

[45] Date of Patent: Oct. 18, 1988

[54] FLUOROACRYLIC MONOMERS AND POLYMERS

[75] Inventors: Marie-José Lina, Tassin La Demi Lune; André Dessaint, Clermont, both of France

[73] Assignee: Atochem, Courbevoie, France

[21] Appl. No.: 920,105

[22] Filed: Oct. 16, 1986

[30] Foreign Application Priority Data

Oct. 16, 1985 [FR] France ............................ 85 15347

[51] Int. Cl.$^4$ ........................................... C07C 127/19
[52] U.S. Cl. ...................................... 560/29; 428/421; 525/276; 526/242; 544/390; 558/232; 558/240; 558/241; 560/27; 560/115; 560/159; 560/220; 560/221; 560/227
[58] Field of Search ............. 560/13, 10, 26, 27, 560/28, 29, 220, 221, 222, 115, 159; 558/240, 232, 241; 544/390

[56] References Cited

U.S. PATENT DOCUMENTS

| | | | |
|---|---|---|---|
| 3,321,445 | 5/1967 | Lazerte et al. | 260/75 |
| 3,468,924 | 9/1969 | Gale | 260/453 |
| 3,503,915 | 3/1970 | Peterson | 260/29.2 |
| 3,528,849 | 9/1970 | Vullo et al. | 117/139.5 |
| 3,839,417 | 10/1974 | Waldmann | 260/481 C |
| 3,869,465 | 4/1975 | Waldmann | 260/29.6 F |
| 3,896,035 | 7/1975 | Schultz et al. | 252/8.75 |
| 3,896,251 | 7/1975 | Landucci | 428/290 |
| 3,899,484 | 8/1975 | Walter | 560/29 |
| 3,906,049 | 9/1975 | Hager | 560/29 |
| 3,929,854 | 12/1975 | Waldmann | 260/458 |
| 4,024,178 | 5/1977 | Landucci | 260/472 |
| 4,287,083 | 9/1981 | McDowell | 560/26 |
| 4,289,892 | 9/1981 | Soch | 560/29 |
| 4,504,401 | 3/1985 | Matsuo et al. | 252/8.75 |
| 4,508,916 | 4/1985 | Newell | 560/26 |
| 4,525,305 | 6/1985 | Patel | 560/26 |
| 4,584,143 | 4/1986 | Falk | 558/240 |

FOREIGN PATENT DOCUMENTS

| | | |
|---|---|---|
| 1071225 | 3/1972 | Canada . |
| 895313 | 2/1980 | Canada . |
| 103752 | 3/1984 | European Pat. Off. . |
| 1620965 | 5/1970 | Fed. Rep. of Germany . |
| 2415150 | 10/1975 | Fed. Rep. of Germany ........ 560/26 |
| 2062244 | 6/1971 | France . |
| 2144204 | 2/1973 | France . |
| 512624 | 10/1971 | Switzerland . |
| 520813 | 5/1972 | Switzerland . |

OTHER PUBLICATIONS

Monbaliu, Res. Discl., 265 pp. 248–250 (1986).

Primary Examiner—Michael L. Shippen
Attorney, Agent, or Firm—Pennie & Edmonds

[57] ABSTRACT

The invention relates to fluoroacrylic monomers of formula:

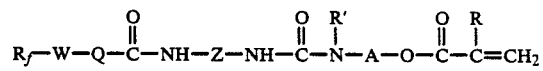

in which $R_f$ denotes a perfluoroalkyl radical, R is hydrogen or a methyl radical, R' denotes an alkyl or cycloalkyl radical, or —NR'— denotes a 1, 4-piperazinylene radical, W and Z denote divalent connecting groups, Q is oxygen or sulphur or an —NR"— group, R" denoting hydrogen an alkyl radical, and A is a $C_2$ or $C_3$ alkylene group. The polymers (homo- or copolymers) derived from these monomers may be used for the water-repellency and oil-repellency treatment of various substrates, particularly leather.

6 Claims, No Drawings

FLUOROACRYLIC MONOMERS AND POLYMERS

TECHNICAL FIELD

The present invention relates to the field of fluorinated products intended for the water-repellency and oil-repellency treatment of substrates such as textiles moquette carpets, wall coverings, wood, building materials, metals, plastics, and its subject is especially products which can be used more particularly for protecting leather whose finish and maintenance should have the following characteristics: suppleness, pleasant appearrance and feel.

BACKGROUND ART

The use of fluoroacrylic resins in these types of applications is well known, but current compounds have a number of disadvantages: a slightly sticky feel, poor cleaning and abrasion resistance and slight alteration in the appearance of the substrate.

Compositions comprising perfluoro groups and urethane linkage have already been proposed; see, for example, the following patents: U.S. Pat. Nos. 3,468,924, 3,503,915, 3,528,849, 3,896,035, 3,896,251 and 4,024,178 FR No. 2,062,244, DE No. 1,620,965, CA No. 1,071,225, EP No. 103,752 and CH No. 520,813 and 512,624. Unfortunately, these products are not always satisfactory, either because the synthesis of the intermediates is diffiult, or because they must be combined with acrylic copolymers because they are not film-forming, do not withstand dry cleaning and/or do not have good stainrepellent properties, or alternatively because they must be supplied as an aqueous emulsion because of their low solubility in solvents.

A new class of fluoroacrylic monomers has now been discovered, whose polymers have outstanding water-repellency and oil-repellency properties and are perfectly adapted to the treatment of leather because of the mechanical properties of their films (adhesion to the substrate, transparency and abrasion resistance).

SUMMARY OF THE INVENTION

The fluoroacrylic monomers according to the present invention, which simultaneously contain a urethane linkage and a urea linkage or two urea linkages, may be denoted by the general formula:

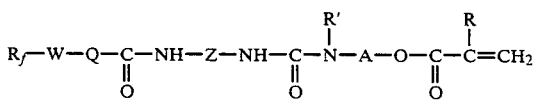

in which:
$R_f$ denotes a straight- or branched-chain perfluoroalkyl radical,
R denotes hydrogen or a methyl radical
R' denotes an alkyl or cycloalkyl radical or —NR' denotes 1,4-piperazinylene radical,
W denotes a divalent linking group attached to Q via a carbon atom and capable of containing one or more oxgen, sulphur and/or nitrogen atoms,
Q denotes oxygen or sulphur or an —NR"— group. R" denoting hydrogen or an alkyl radical,
Z denotes a divalent aliphatic, alicyclic or aromatic connecting group and
A denotes an alkylene group containing 2 or 3 carbon atoms.

The perfluoroalkyl radical $R_f$ may contain from 2 to 20 carbon atoms. However, compounds in which $R_f$ is a linear perfluoroalkyl radical containing 6, 8 qr 10 carbon atoms are preferred.

The alkyl radical R' may have a straight or branched chain and may contain from 1 to 12 carbon atoms. Compounds in which R' contains 2 to 4 carbon atoms, and more especially those in which R' is the tert-butyl radical are preferred.

When R" is alkyl, it may contain 1 to 4 carbon atoms. Z may contain from 6 to 14 carbon atoms.

DETAILED DESCRIPTION OF THE INVENTION

The fluoroacrylic monomers of formula (I) according to the invention may be prepared by reacting a diisocyanate of the formula:

$$O=C=N-Z-N=C=O \quad \text{(II)}$$

with substantially equimolar quantities of a polyfluoro compound of the formula:

$$R_f-W-Q-H \quad \text{(III)}$$

and an acrylic ester of the formula:

$$R'-N(H)-A-O-C(O)-C(R)=CH_2 \quad \text{(IV)}$$

As examples of diisocyanates which may be used include aromatic diisocyanates such as 2,4- and/or 2,6-toluene diisocyanate, 4,4'-diphenylmethane diisocyanate and xylylene diisocyanate; aliphatic diisocyanates such as hexamethylene diisocyanate and decamethylene diisocyanate; and alicyclic diisocyanates such as 4,4'-methylene bis(cyclohexyl isocyanate), 2-methyl-1,4-cyclohexane diisocyanate and isophorone diisocyanate. Among these diisocyanates, 2,4-toluene diisocyanate is especially preferred by itself or mixed with the 2,6-isomer.

The polyfluoro compound (III) is a compound containing a mobile hydrogen atom in the form of a terminal hydroxyl, thiol or primary or secondary amino group, attached to the perfluoroalkyl radical directly via, alkylene bridge or indirectly via a concatenation consisting of one or more alkylene bridges and of a sulphonamido, carbonamido, ether, thioether, sulphonyl or carboxylic ester group. As examples of such polyfluoro compounds, the invention particularly includes those of the following formulae:

$$R_f-(CH_2)_p-OH \quad \text{(III-a)}$$

$$R_f-SO_2-\underset{R''}{\underset{|}{N}}-(CH_2)_q-OH \quad \text{(III-b)}$$

$$R_f-(CH_2)_p-SO_2\underset{R''}{\underset{|}{N}}-(CH_2)_q-OH \quad \text{(III-c)}$$

$$R_f-(CH_2)_p-O-(CH_2)_q-OH \quad \text{(III-d)}$$
$$R_f-(CH_2)_p-S-(CH_2)_q-OH \quad \text{(III-e)}$$
$$R_f-(CH_2)_p-(OCH_2CH_2)_q-OH \quad \text{(III-f)}$$
$$R_f-(CH_2)_p-SO_2-(CH_2)_q-OH \quad \text{(III-g)}$$

$$R_f-\underset{\underset{O}{\|}}{C}-\underset{R''}{\underset{|}{N}}-(CH_2)_p-OH \quad \text{(III-h)}$$

-continued

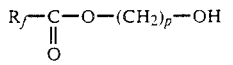   (III-i)

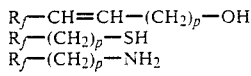   (III-j)
$R_f—(CH_2)_p—SH$   (III-k)
$R_f—(CH_2)_p—NH_2$   (III-l)

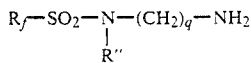   (III-m)

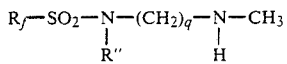   (III-n)

in which $R_f$ and R" have the same meaning as defined above, and the symbols p and q, which can be identical or different, each denote an integer ranging from 1 to 20 and preferably equal to 2 or 4. For economic and practical reasons, it is especially advantageous to use a mixture of compounds representing various radicals $R_f$.

Among the compounds (III), those of formulae (III -a), (III -c) and (III -k), in which p and q are equal to 2, are most especially preferred.

As examples of esters of formula (IV), the acrylic and methacrylic esters of 2-t-butylamino ethanol, 2-t-octylamino ethanol, 2-cyclohexylamino ethanol, 2-laurylaminoethanol and 2-piperazino ethanol have been found to be particularly useful. A preferred compound of formula (IV) is 2-t-butylaminoethyl methacrylate of formula:

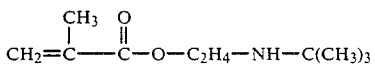   (IV-a)

The synthesis of the fluoroacrylic monomers (I) according to the invention may be carried out in an organic solvent such as ketonic solvents (e.g., methyl ethyl ketone or methyl isobutyl ketone), esters (e.g., ethyl acetate or butyl acetate), aromatic solvents (e.g., toluene, xylene or benzene), alkanes (e.g., hexane, heptane or cyclohexane), ethers (e.g., diisopropyl ether or tetrahydrofuran), halogenated solvents (e.g., 1,1,1-trichloroethane or trichlorotrifluoroethane), dimethylformamide and N-methylpyrrolidone.

The addition reactions of the polyfluoro compound $R_f—W—Q—H$ and of the acrylic ester (IV) to the $—N=C=O$ groups are carried out between 30° and 90° C. under an inert atmosphere, for example under dry nitrogen. Since the addition of the polyfluoro compound is slow, it is preferable to conduct this reaction in the presence of a catalyst such as, for example, a tertiary amine like triethylamine, triethylene diamine and N-methylmorpholine, a tin salt like dibutyltin dilaurate and tin octoate, or a lead salt like lead naphthenate, the catalyst being used in a proportion of 0.05 to 1% based on the total weight of the reactants.

In order to limit the formation of symmetrical diaddition products, the perfluoro compound $R_f—W—Q—H$ is added dropwise, under dilution and temperature conditions such that the reaction is virtually instantaneous and that there is always a deficiency of $R_f—W—Q—H$ relative to the isocyanate (i.e., an excess of isocyanate). The acrylic ester bearing the more active —NH group is added in a second step. It reacts very readily with the remaining free—$N=C=O$ groups. The formation of symmetrical diaddition compounds cannot be avoided altogether; but it is possible, if desired, to remove them by filtration, since their solubility in the reaction solvents is lower than that of the urethane/urea monomers of formula (I).

The invention also relates to the polymers containing repeat units of formula:

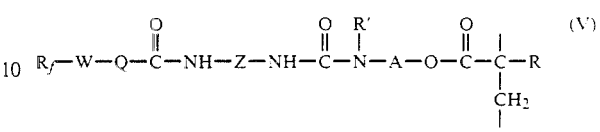   (V)

in which the various symbols have the same meanings as defined above. These polymers may be prepared from the monomers of formula (I) by homopolymerization or by copolymerization with other monomers (fluorinated or otherwise) in a proportion ranging up to 90% by weight based on the total weight of monomers.

As examples of comonomers which may be used within the scope of the present invention, the following are included:

lower (halogenated or otherwise) olefinic hydrocarbons such as ethylene, propylene, isobutene, 3-chloro-1-isobutene, butadiene, isoprene, chloro- and dichlorobutadiene, fluoro- and difluorobutadienes, 2,5-dimethyl-1,5-hexadiene and diisobutylene;

vinyl, allyl or vinylidene halides such as vinyl or vinylidene chloride, vinyl or vinylidene fluoride, allyl bromide and methallyl chloride;

styrene and its derivatives, such as vinyltoluene, α-methylstyrene, α-cyanomethylstyrene divinyl benzene and N-vinylcarbazole;

vinyl esters such as vinyl acetate, vinyl propionate, vinyl esters of acids known commercially under the name of "Versatic Acids", vinyl isobutyrate, vinyl senecioate, vinyl succinate, vinyl isodecanoate, vinyl stearate and divinyl carbonate;

allyl esters such as allyl acetate and allyl heptanoate;

alkyl vinyl ethers or alkyl allyl ethers (halogenated or otherwise), such as cetyl vinyl ether, dodecyl vinyl ether, isobutyl vinyl ether, ethyl vinyl ether, 2-chloroethyl vinyl ether and tetraallyl oxy ethane;

vinyl alkyl ketones such as vinyl methyl ketone;

unsaturated acids such as acrylic, methacrylic, α-chloroacrylic, crotonic, maleic, fumaric, itaconic, citraconic and senecioic acids, their anhydrides and their esters such as vinyl, allyl, methyl, butyl, isobutyl, hexyl, heptyl, 2-ethylhexyl, cyclohexyl, lauryl, stearyl or alkoxy ethyl acrylates and methacrylates, dimethyl maleate, ethyl crotonate, methyl hydrogen maleate, butyl hydrogen itaconate, glycol or polyalkylene glycol diacrylates and dimethacrylates such as ethylene glycol dimethacrylate or triethylene glycol dimethacrylate, dichlorophosphatoalkyl acrylates and methacrylates such as dichlorophosphatoethyl methacrylate, and bis(methacryloyloxyethyl) hydrogen phosphate and methacryloyloxy propyltrimethoxysilane;

acrylonitrile, methacrylonitrile, 2-chloroacrylonitrile, 2-cyanoethyl acrylate, methyleneglutaronitrile, vinylidene cyanide, alkyl cyanoacrylates such as isopropyl cyanoacrylate, tris(acryloyl)hexahydro-s-triazine, vinyltrichlorosilane, vinyltrimethoxysilane, vinyltriethoxysilane and N-vinyl-2-pyrrolidone;

allyl alcohol, allyl glycolate, isobutenediol, allyloxyethanol, o-allylphenol, divinylcarbinol, glycerol allyl ether, acrylamide, methacrylamide, maleamide and maleimide, N-(cyanoethyl)acrylamide, N-isopropyl acrylamide, diacetoneacrylamide, N-(hydroxymethyl) acrylamide and methacrylamide, N-(alkoxymethyl)acrylamides and methacrylamides, glyoxal bisacrylamide, sodium acrylate or methacrylate, vinylsulphonic and styrene-p-sulphonic acids and their alkali metal salts, 3-amino-crotononitrile, monoallylamine, vinylpyridines, glycidyl acrylate or methacrylate, allyl glycidyl ether, acrolein, N,N-dimethylaminoethyl methacrylate or N-tert-butylamino ethyl methacrylate; and the unsaturated fluoroesters of general formula:

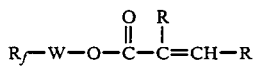

(VI)

in which $R_f$, R and W have the same meanings as defined above. These comonomers may be prepared by known methods, for example by esterification of the corresponding polyfluoro alcohols of formula:

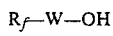

(VII)

by means of an alkenemonocarboxylic acid of formula:

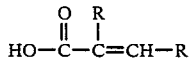

(VIII)

such as, for example, acrylic acid, methacrylic acid or crotonic acid, in the presence of a catalyst such as sulphuric acid or p-toluenesulphonic acid. Instead of the acids of formula (VIII), it is also possible to use their esters, anhydrides or halides As examples of polyfluoro alcohols of formula (VII), there may be more particularly mentioned those of formulae (III a) to (III j).

Comonomers which may also be employed in the present invention include:

the unsaturated esters of formula:

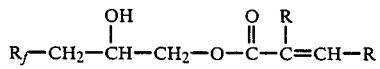

(IX)

obtained by condensation of a fluoro epoxide:

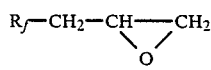

(X)

with an alkene monocarboxylic acid of formula (VIII); and acrylates and methacrylates of ethers of polyethylene glycols or of polypropylene glycols of formula:

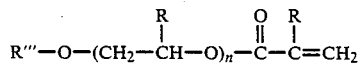

(XI)

in which R denotes hydrogen or a methyl radical, R''', denotes an alkyl radical and n is an integer from 2 to 10.

The fluoropolymers according to the invention may be prepared by a method which is known per se by polymerization in an organic solvent or in aqueous emulsion, at a temperature which may range from ambient to the boiling point of the reaction medium. The process is usually carried out between 70° and 110° C. The total monomer concentration may vary from 5 to 60% by weight.

The polymerization in a solvent medium may be performed in ketonic solvents (e.g., acetone, methyl ethyl ketone, methyl isobutyl ketone), alcohols (e.g., isopropanol), esters (e.g., ethyl acetate or butyl acetate), ethers (e.g., diisopropyl ether, ethyl or methyl ethylene glycol ether, tetrahydrofuran, dioxane), aliphatic or aromatic hydrocarbons, halogenated hydrocarbons (e.g., perchloroethylene, 1,1,1-trichloroethane or trichlorotrifluoroethane), dimethyl formamide or N-methyl-2-pyrrolidone.

The polymerization is carried out in the presence of initiator(s) used in a proportion of 0 1 to 1.5% based on the total weight of the monomers employed. It is possible to use as initiators peroxides such as, for example, benzoyl peroxide, lauroyl peroxide, succinyl peroxide and tert-butyl perpivalate, or azo compounds such as, for example, 2,2'-azobisisobutyronitrile, 4,4,-azobis(4-cyanopentanoic acid) and azodicarbonamide. It is also possible to operate in the presence of UV radiation and of photoinitiators such as benzophenone, 2-methylanthraquinone or 2-chlorothioxanthone. If required, the length of the polymer chains may be regulated by means of chain transfer agents such as alkyl mercaptans, carbon tetrachloride or triphenylmethane, used in a proportion of 0.05 to 0.5% based on the total weight of monomers.

The polymerization in aqueous emulsion may be carried out according to well-known methods, noncontinuously or continuously. The surface-active agents to be used for emulsifying may be cationic, anionic or nonionic, depending on the required ionicity of the final latex, and are preferably chosen from the best oil-in-water emulsifiers which wet as little as possible. Pairs of cationic/nonionic or anionic/ nonionic surfactants are preferably used. Examples of surface-active agents which may be used include: in the cationic series, salts of long-chain tertiary amines such as N,N-dimethyloctadecylamine acetate, and quaternary ammonium salts of fatty amines such as trimethylcetylammonium bromide or trimethyldodecyl ammonium chloride;

in the anionic series, the alkali metal salts of long-chain alkylsulphonic acids and alkali metal arylalkylsulphonates;

in the nonionic series, the condensation products of ethylene oxide with fatty alcohols or alkyl phenols.

It may also be advantageous to use surface-active agents containing a perfluorinated water-repellent chain such as, for example, ammonium perfluorooctanoate or potassium N-perfluorooctyl sulphonyl-N-ethylamino acetate.

To make it easier to emulsify the monomers, it is generally necessary to use organic solvents such as, for example, ketones (acetone, methyl ethyl ketone, methyl isobutyl ketone), glycols or ethylene glycol ethers, alcohols (methanol, ethanol, isopropanol), or mixtures of these solvents. In general, the quantity of solvent should not exceed the total weight of the monomers.

Water-soluble products such as inorganic peroxddes (for example hydrogen peroxide) and persalts (for example potassium persulphate), or water-insoluble initiators such as organic peroxides and the azo compounds referred to earlier may be used as polymerization initiators in an aqueous emulsion.

The fluoropolymers according to the invention may also be prepared by grafting a fluoro isocyanate-urethane of

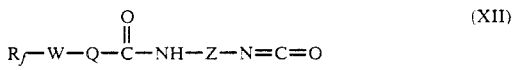

$$R_f-W-Q-\overset{O}{\underset{\|}{C}}-NH-Z-N=C=O \quad \text{(XII)}$$

onto an acrylic polymer containing pendent —NH groups, produced by homopolymerization of an acrylic ester of formula (IV) or by copolymerization of such an ester with one or more of the comonomers referred to earlier. The isocyanatesurethanes of formula (XII) may be prepared in the same manner and under the same conditions as the monomers of formula (I) by reacting a diisocyanate (II) with a substantially equimolar quantity of a polyfluorinated compound (III). These operating conditions also apply to the grafting of the isocyanate-urethane (XII) onto the acrylic polymer containing pendent —NH groups. This polymer may itself be obtained by polymerization in a solvent medium under conditions which are similar to those described earlier for the polymerization of monomers of formula (I).

Whatever the method by which they are obtained, the fluoropolymers according to the invention may be isolated, if appropriate, by following methods which are known per se such as, for example, precipitation or evaporation of the solvent.

The fluoropolymers according to the invention are found to be outstanding water-repellent and oil-repellent agents on very diverse materials such as paper, non-woven articles, textiles based on natural artificial or synthetic fibres, plastics, wood, metals, glass, stone and cement, but are more particularly intended for the protection of leathers, where their finish is involved, or for the maintenance of leather articles such as clothes, shoes, leather goods, seats, etc.

For application to the substrate, the polymer solutions are generally diluted with a solvent identical to or compatible with that used for the polymerization, while the polymer emulsions are diluted with water. Application of the diluted products may be carried out by following various methods such as spraying, brush-coating or padding. Depending on their nature, the treated substrates may be dried at ambient temperature or at temperatures which may range up to 200° C.

The quantity of polymer to be employed may vary within wide limits, depending on the nature of the substrate and of the fluorine content of the polymer. On leather, this quantity is generally between 1 and 10 g/m².

EXAMPLES

The following examples, in which, unless stated otherwise, the parts and the percentages are on a weight basis, illustrate the invention without limiting it.

EXAMPLE 1

370 parts of dry methyl isobutyl ketone and 69.6 parts (0.4 mole) of toluene diisocyanate (mixture of 80% 2,4-isomer and 20% 2,6-isomer) and 0.4 part of dibutyltin dilaurate are charged into a reactor of a capacity of 1000 parts by volume, fitted with a stirrer, a thermometer, a reflux condenser, a dropping funnel, a nitrogen inlet and a heating device. Air is purged from the reactor with a stream of dry nitrogen, and then the temperature of the reaction mixture is raised to 80° C. by means of a thermostated oil bath and a solution, dried beforehand by distillation, containing 145.6 parts of perfluorohexyl ethanol $C_6F_{13}C_2H_4OH$ (0.4 mole) and 145.6 parts of methyl isobutyl ketone, is then added dropwise over one hour. The mixture is kept stirred at 80° C. for ½ hour. Analysis by chromatography (GPC) shows that the reaction has ended and that 25% of a symmetrical diaddition product has formed. 0.120 part of hydroquinone monomethyl ether is then added, and a solution of 74 parts of t-butylaminoethyl methacrylate (0.4 mole) in 74 parts of methyl isobutyl ketone is added at 80° C. over 10 min. The mixture is kept at 80° C. for 1 h 30 min and is then cooled. 875 parts of a yellow solution $(S_1)$ of a monomer according to the invention are obtained in this manner. This solution contains 33% solids and partially crystallizes when stored cold.

EXAMPLE 2

125 parts of solution $S_1$ are charged into a reactor of a capacity of 250 parts by volume, fitted with a stirrer, a thermometer, a reflux condenser, a nitrogen inlet and a heating device. After its surface has been purged with nitrogen, the solution is heated to 90° C. and 0.3 part of lauroyl peroxide and 0.2 part of t-butyl perpivalate are then added. The temperature is then maintained at 90° C. for 6 hours, the same quantity of initiators being added after 2 and 4 hours. Analysis by chromatography shows complete disappearance of the monomer. After cooling, 124 parts of a yellow-brown solution $(S_2)$ of homopolymer according to the invention are obtained. This solution contains 33.1% solids and 11.3% of fluorine

EXAMPLE 3

17.4 parts of toluene diisocyanate (0.1 mole), 88 parts of dry methyl isobutyl ketone and 0.1 part of dibutyltin dilaurate are charged into a reactor of a capacity of 500 parts by volume, fitted as that of Example 1. The atmosphere in the reactor is made inert with a stream of dry nitrogen and then the temperature is raised to 80° C. A solution, dried by distillation, of 36.4 parts of perfluorohexylethanol (0.1 mole) in 36.4 parts of methyl isobutyl ketone is then added dropwise over 40 min. The reaction is complete ten minutes after the end of the addition. A solution of 18.5 parts of tert-butylaminoethyl methacrylate (0.1 mole) in 18.5 parts of dry methyl isobutyl ketone is then added over 5 min and the temperature is maintained at 80° C. for another 15 min. 72.3 parts of 2-ethylhexyl methacrylate and 74.4 parts of methyl isobutyl ketone are then added and the temperature of the solution is raised to 90° C. Polymerization is initiated by adding 0.6 part of lauroyl peroxide and 0.4 part of t-butyl perpivalate and maintained by adding the same quantities of initiators at two-hourly intervals. After 6 hours the solution is cooled and filtered. A copolymer according to the invention is thus obtained, containing 50% of urethane-urea monomer and 50% of ethylhexyl methacrylate, in the form of a viscous, amber-yellow solution $(S_3)$ which contains 39% solids and 6.64% of fluorine.

EXAMPLE 4

Into a reactor which is identical to that of Example are added 88.65 parts of solution $(S_1)$ containing 33% of urethane-urea monomer, 9 parts of butyl methacrylate, 11.35 parts of a mixture of polyfluoro monomers of the formula:

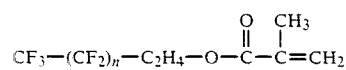

$$CF_3-(CF_2)_n-C_2H_4-O-\overset{O}{\underset{\|}{C}}-\overset{CH_3}{\underset{|}{C}}=CH_2$$

where n is equal to 5, 7, 9, 11, 13 and 15 in mean proportions by weight of 1:56:22:9:3:3 respectively, and 11.4 parts of methyl isobutyl ketone. Air is purged from the reactor with a stream of nitrogen for 15 min and then the temperature is raised to 90° C. 0.3 part of lauroyl peroxide and 0.2 part of t-butyl perpivalate are then added, this addition being repeated at two-hourly intervals. The polymerization is complete after 6 hours. The yellow-brown solution is filtered at 40° C. When cold, a fluid gel (S$_4$) is obtained, which contains 42% nonvolatiles and 15.5% of fluorine.

EXAMPLE 5

Into a reactor which is identical to that of Example 2 are added 88.65 parts of solution (S$_1$) containing 33% of urethane-urea monomer, 9 parts of 2-ethyl hexyl methacrylate, 16 parts of polyfluoro monomers of formula:

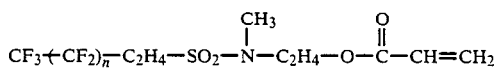

where n=3, 5, 7, 9, 11, 13 and 15 in mean proportions by weight of 1:50:31:10:3:1:1 respectively, together with 4.4 parts of acetone and 7 parts of methyl isobutyl ketone. Polymerization is then carried out as in Example 4 and a yellow-brown gel (S$_5$) is obtained, whose nonvolatiles content is 42.6% and the fluorine content is 13.5%.

EXAMPLE 6

A solution containing 92.8 parts of perfluorooctylethanol C$_8$F$_{17}$C$_2$H$_4$OH (0.2 mole) and 92.8 parts of methyl isobutyl ketone is added dropwise over one hour and at 80° C., to a solution of 34.8 parts (0.2 mole) of toluene diisocyanate (mixture containing 80% of 2,4- and 20% of 2,6-isomer), 0.2 part of dibutyltin dilaurate and 254 parts of methyl isobutyl ketone, in a reactor identical to that in Example 1 and using the same operating procedure. 37 parts of t-butylaminoethyl methacrylate (0.2 mole) in 37 parts of methyl isobutyl ketone are then added, still at 80° C. After 1 h 30 min at 80° C., the reaction has ended and a solution (S$_6$) of urethane-urea monomer according to the invention is obtained. This solution contains 30% solids and 11.78% of fluorine.

EXAMPLE 7

83.3 parts of the solution (S$_6$), 18 parts of methyl isobutyl ketone and 25 parts of butyl methacrylate are introduced into a reactor identical to that in Example 2. After the reactor has been purged with nitrogen, the temperature is raised to 90° C. and 0.3 part of lauroyl peroxide and 0.2 part of t-butyl perpivalate are added. The mixture is heated at 90° C. for 6 hours while polymerization is maintained by adding the same charge of initiators at two-hourly intervals. The copolymer solution obtained (S$_7$) is homogeneous, but is opaque and viscous. It contains 39.3% nonvolatiles and 7.7% of fluorine.

EXAMPLE 8

The method of Example 1 is followed. A previously topped solution of 48.5 parts of a fluorinated sulphamidoalcohol of formula

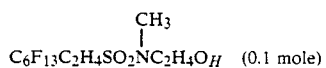

in 37.7 parts of methyl isobutyl ketone is added dropwise over one hour and at 80° C., to a mixture of 17.4 parts of toluene diisocyanate (0.1 mole), 0.1 part of dibutyltin dilaurate and 140 parts of methyl isobutyl ketone. 0.030 part of hydroquinone methyl ether and 18.5 parts of t-butylaminoethyl methacrylate (0.1 mole) are then added and the mixture is maintained at 80° C. for another 2 hours. A solution (S$_8$) of urethane-urea monomer according to the invention is obtained in this manner, containing 30% solids and 8.8% of fluorine.

EXAMPLE 9

The method of Example 7 is used to copolymerize 83.4 parts of solution (S$_8$) with 25 parts of stearyl methacrylate in 17 parts of methyl isobutyl ketone. The yellow-brown solution obtained (S$_9$) contains 39.5% of nonvolatiles and 5.8% of fluorine.

EXAMPLE 10

The method of Example 8 is followed, the fluorinated sulphamidoalcohol being replaced by 48 parts of perfluorooctylthioethanol C$_8$F$_{17}$C$_2$H$_4$SH (0.1 mole). The solution (S$_{10}$) obtained contains 30% nonvolatiles and 11.5% of fluorine.

EXAMPLE 11

83.4 parts of solution (S$_{10}$) are copolymerized under the same conditions as in Example 7 with 25 parts of 2-ethylhexyl methacrylate in 17 parts of methyl isobutyl ketone. The yellow-brown solution (S$_{11}$) obtained contains 35.5% nonvolatiles and 6.8% of fluorine.

EXAMPLE 12

By using the same procedure as in Example 7, 83.4 parts of solution (S$_8$) are copolymerized with 9 parts of stearyl methacrylate and 16 parts of a fluoroacrylic ester of formula:

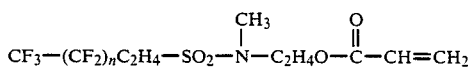

where n is equal to 3, 5, 7, 9, 11, 13 and 15 in mean weight proportions of 1:50:31:10:3:1:1 respectively, in 13 parts of methyl isobutyl ketone and 4 parts of acetone. A yellow-brown solution (S$_{12}$), inhomogeneous when cold, is obtained, containing 40.4% non-volatiles and 11.9% of fluorine.

EXAMPLE 13

13-a: By following the same method as in Example 7, a copolymer is prepared which is based on 18.5 parts of t-butylaminoethyl methacrylate (0.1 mole), 49.3 parts of butyl methacrylate and 55.5 parts of a mixture of fluoroalcohol methacrylates of formula:

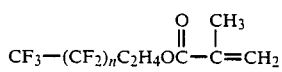

where n=5, 7, 9, 11, 13 and 15 in mean proportions by weight of 1:56:22:9:3:3 respectively, in 125 parts of methyl isobutyl ketone.

13-b Proceeding as in Example 1, 72.8 parts of a solution containing 50% of perfluorohexyl ethanol $C_6F_{13}C_2H_4OH$ (0.1 mole) in methyl isobutyl ketone are added over one hour at 80° C. to 17.4 parts of toluene diisocyanate (containing 80% 2,4- and 20% 2,6-isomer) in 110 parts of methyl isobutyl ketone.

13-c: The polymer 13-a containing pendent —NH groups is added to the isocyanate-urethane obtained in 13-b. The mixture is then heated to 100° C. for 2 hours. A solution ($S_{13}$) of a copolymer according to the invention is obtained in this manner. This yellow-brown solution, slightly viscous, contains 38.4% nonvolatiles and 12.8% of fluorine.

EXAMPLE 14

The polymer solutions $S_2$, $S_3$, $S_4$, $S_5$, $S_7$, $S_9$, $S_{11}$, $S_{12}$ and $S_{13}$ are diluted with methyl isobutyl ketone so as to produce solutions $S_{2d}$, $S_{3d}$, $S_{4d}$, $S_{5d}$, $S_{7d}$, $S_{9d}$, $S_{11d}$, $S_{12d}$ $S_{13d}$, each containing 0.15% of fluorine. These dilute solutions are then applied by spraying onto a vegetable tanned full grain kip leather, at a rate of 200 g/m and are left to dry for 4 hours at ambient temperature before the following tests are carried out:

W.P. TEST (water penetration): consists in measuring the penetration time of a drop of water deposited on the leather.

O.P. TEST (oil penetration): consists in measuring the penetration time of a drop of paraffin oil deposited on the leather.

The results obtained are collated in the following table, compared with the same leather untreated.

| Treatment solution | Water-repellency W.P. | Oil-repellency O.P. |
|---|---|---|
| Nil (untreated leather) | Less than 30 seconds | Less than 10 seconds |
| $S_{2d}$ | 5.5 hours | 20 minutes |
| $S_{3d}$ | 6.5 " | 50 minutes |
| $S_{4d}$ | 8 " | more than 24 hours |
| $S_{5d}$ | 8.5 " | more than 9 hours |
| $S_{7d}$ | 3.5 " | 30 minutes |
| $S_{9d}$ | 7.5 " | more than 24 hours |
| $S_{11d}$ | 4.5 " | 1 hour |
| $S_{12d}$ | 5.5 " | more than 24 hours |
| $S_{13d}$ | 1 hour | 3 hours |

EXAMPLE 15

92.5 parts of methyl isobutyl ketone, 17.4 parts (0.1 mole) of toluene diisocyanate (containing 80% of 2,4- and 20% of 2,6-isomer) and 0.1 part of dibutyltin dilaurate are introduced into a reactor of 250 parts by volume capacity, fitted with a stirrer, a thermometerm a reflux condenser, a dropping funnel and a heating system (thermostated oil bath). The solution is heated to 80° C. in a nitrogen atmosphere, and then a mixture of 36.4 parts of perfluorohexylethanol $C_6F_3C_2H_4OH$ (0.1 mole), 18.5 parts of t-butylaminoethyl methacrylate (0.1 mole) and 54 parts of dry methyl isobutyl ketone are added dropwise over one hour. The solution is kept at 80° C. for another 2 hours and a mixture is thus obtained, containing mostly the addition product of t-butylaminoethyl methacrylate in the 2 position and of perfluorohexylethanol in the 4 and 6 positions, together with a molar proportion of 42% of products of symmetrical diadditions. This mixture is heated to 90° C. and 0.5 part of lauroyl peroxide and 0.2 part of t-butyl perpivalate are then added to it and this addition of initiators is repeated after 2 and 4 hours reaction. After 6 hours at 90 the reaction is finished. The solution ($S_{15}$) obtained is yellow-brown and clear; it contains 32.8% nonvolatiles and 11.2% of fluorine.

This solution is diluted with methyl isobutyl ketone to a fluorine content of 0.15% and is then applied to the same leather as in Example 14 at a rate of 200 g/m². After drying overnight at ambient temperature, the following results are obtained:

W.P. = 7.5 hours and O.P. = 30 minutes

EXAMPLE 16

180 parts of trichlorotrifluoroethane, 34.8 parts (0.2 mole) of toluene diisocyanate (mixture containing 80% of 2,4-isomer and 20% of 2,6-isomer) and 0.2 parts of dibutyltin dilaurate are introduced into a reactor which is identical to that in Example 1. After the air in the reactor has been purged with a stream of dry nitrogen and the temperature has been raised to 50° C. (solvent reflux), a solution of 72.8 parts of perfluorohexylethanol $C_6F_{13}C_2H_4OH$ in 72.8 parts of trichlorotrifluoroethane are added dropwise over an hour and a quarter. Refluxing is then maintained for ½ hour and a whitish suspension is obtained, whose analysis by chromatography shows that it contains a molar proportion of approximately 20% of 2,4- and 2,6-diaddition product. 0.06 part of hydroquinone methyl ether is then added to the whitish suspension obtained, and 37 parts of t-butylaminoethyl methacrylate (0.2 mole) are then run in over 15 minutes, followed by 40 parts of trichlorotrifluoroethane. The reaction is slightly exothermic and the whitish product is seen to dissolve. Refluxing is maintained for one hour and then 293 parts of isopropanol are added and the trichlorotrifluoroethane is removed by distillation. A practically colourless solution ($S_{16}$) is obtained, containing 33% nonvolatiles and 11.3% of fluorine.

EXAMPLE 17

Into a reactor of 500 parts by volume capacity, fitted out as that in Example 2, are introduced 25 parts of a mixture of polyfluoro monomers of formula:

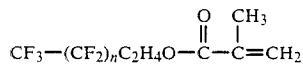

where n is equal to 5, 7, 9, 11, 13 and 15 in mean weight proportions of 1:56:22:9:3:3 respectively, 20 parts of methoxytriethylene glycol methacrylate:

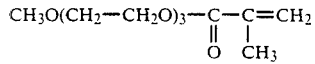

5.15 parts of the solution and 50 parts of isopropyl alcohol. After air has been purged from the reactor with a stream of nitrogen, the mixture is heated to 82° C. and 0.5 part of 4,4'-azobis(4-cyanopentanoic acid) is added. Refluxing is maintained for 5 hours, 0.1 part of tert-butyl perpivalate being added every hour. 50 parts of a 50/50 mixture by weight of isopropanol and water are then added. After cooling and filtration, a solution ($S_{17}$) is obtained, which contains 30.7% nonvolatiles and 10.5% of fluorine.

A part of this solution is diluted to 100 with a 50/50 mixture of water and isoproopanol and the clear solution obtained ($S_{17d}$) is applied by spraying to two types of leather, at a rate of 400 g/m². These are allowed to dry for four hours at ambient temperature before assessment of performance is carried out using the method indicated earlier. Results are shown below in Table II.

| Material | W.P. | O.P. |
|---|---|---|
| Chrome-tanned full grain kip leather Untreated | Less than 30 seconds | Less than 1 minute |
| Same Leather treated with $S_{17d}$ | 2.25 hours | More than 9 hours |
| Vegetable-tanned full grain kip leather Untreated | Less than 30 seconds | Less than 10 seconds |
| Same Leather treated with $S_{17d}$ | 3.25 hours | More than 9 hours |

EXAMPLE 18

Example 3 is repeated with the following modifications;

(a) Toluene diisocyanate is repalced by 25 parts of 4,4′-diphenylmethane diisocyanate (0.1 mole) and the initial amount of methyl isobutyl ketone is increased to 132 parts;

(b) In the polymerization step, 79.9 parts of 2-ethylhexyl methacrylate and only 53 parts of methyl isobutyl ketone are used, while initiation is effected with 1 part of lauroyl peroxide and 0.6 part of t-butyl perpivalate.

After 6 hours, the solution is cooled. A copolymer according to the invention is thus obtained, based on 50% of urethane-urea monomer and 50% of 2-ethylhexyl methacrylate, in the form of a thick solution ($S_{18}$) which cfontains 40% of non volatiles and 6% of fluorine.

This solution is diluted with perchloroethylene to a fluorine content of 0.15% and is then applied at the rate of 200 g/m² onto vegetable tanned full grain kip leather. Results of the tests are as follows:

W.P.: more than 9 hours.
O.P.: more than 30 hours.

While it is apparent that the invention herein disclosed is well calculated to fulfill the objects above stated, it will be appreciated that numerous modifications and embodiments may be devised by those skilled in the art, and it is intended that the appended claims over all such modifications and embodiments as fall within the true spirit and scope of the present invention.

What is claimed is:

1. Fluoroacrylic monomers of the formula:

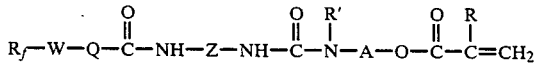

in which:
$R_f$ is a straight or branched chain perfluoroalkyl radical;
R is a hydrogen or a methyl radical,
R′ is an alkyl or cycloalkyl radical, and, alternately, —NR′— denotes a 1,4-piperazinylene radical,
W—Q is selected from among —(CH$_2$)$_p$—O—, —(CH$_2$)$_p$—S—, —(CH$_2$)$_p$—NH—, —(CH$_2$)$_p$—SO$_2$N(R″)—(CH$_2$)$_q$—O—, —SO$_2$—N(R′′)—(CH$_2$)$_q$—O—, —(CH$_2$)$_p$—O—(CH$_2$)$_q$—O—, —(CH$_2$)$_p$—S—(CH$_2$)$_q$—O—, —(CH$_2$)$_p$—(OCH$_2$CH$_2$)$_q$—O—, —(CH$_2$)$_p$—SO$_2$—(CH$_2$)$_q$—O—, —CO—N(R″)—(CH$_2$)$_p$—O—, —CO—O—(CH$_2$)$_p$—O—, —CH=CH—(CH$_2$)$_p$—O—, —SO$_2$—N(R″)—(CH$_2$)$_q$—NH and —SO$_2$—N(R″)—(CH$_2$)$_q$—NCH$_3$—divalent linkages, wherein R″ is hydrogen or an alkyl radical and p and q each represent an integer ranging between 1 and 20, inclusive,
Z is a divalent aliphatic, alicyclic or aromatic connecting group, and
a is an alkylene group having 2 or 3 carbon atoms.

2. The monomers according to claim 1, in which A is an ethylene group, R′ is a tert-butyl radical and Z is a 2,4- and/or 2,6-tolylene group.

3. The monomers according to claim 1, in which $R_f$ is a linear perfluoroalkyl radical containing 6, 8 or 10 carbon atoms.

4. Fluoroacrylic monomers of the formula

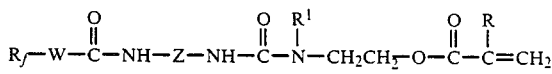

in which
$R_f$ is a perfluoroalkyl radical of 6, 8 or 10 carbon atoms,
R is hydrogen or a methyl radical,
R′ is a tert-butyl radical,
W is a —CH$_2$CH$_2$—O—, —CH$_2$CH$_2$—S—, or —CH$_2$CH$_2$—SO$_2$—N(R″)—CH$_2$CH$_2$—O—°linking group,
R″ is hydrogen or an alkyl radical, and
Z is a 2,4- and/or 2,6-tolylene group.

5. Fluoroacrylic monomers of the formula:

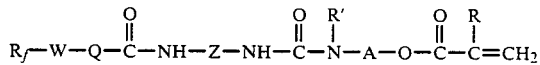

in which:
$R_f$ is a straight or branched chain perfluoroalkyl radical,
R is a hydrogen or a methyl group,
R′ is an alkyl or cycloalkyl radical and, alternately, —NR′— denotes a 1,4 piperazinylene radical,
W—Q is selected from among —CH$_2$CH$_2$—O—, CH$_2$CH$_2$—S— and —CH$_2$CH$_2$—SO$_2$—N(R′)—CH$_2$CH$_2$—O—,
R″ is a hydrogen or an alkyl radical,
Z is a divalent aliphatic, alicyclic or aromatic connecting group, and
A is an alkylene group having 2 or 3 carbon atoms.

6. The monomers according to claim 5 in which A is ethylene, R′ is tert-butyl and Z is 2,4- and/or 2,6 tolylene.

* * * * *